United States Patent [19]

Inoue et al.

[11] Patent Number: 5,386,816
[45] Date of Patent: Feb. 7, 1995

[54] ENDOSCOPE

[75] Inventors: Masahiro Inoue; Kunihiko Miyagi, Tokyo, both of Japan

[73] Assignee: Kabushiki Kaisha Machida Seisakusho, Tokyo, Japan

[21] Appl. No.: 950,155

[22] Filed: Sep. 24, 1992

[30] Foreign Application Priority Data

Oct. 4, 1991 [JP] Japan ................. 3-283928

[51] Int. Cl.6 ............................................. A61B 1/00
[52] U.S. Cl. ........................................ 128/4; 138/118
[58] Field of Search ................. 128/4, 6, ; 138/118, 138/118.1, 120, 123, 155; 604/282, 264

[56] References Cited

U.S. PATENT DOCUMENTS

| | | | |
|---|---|---|---|
| 4,805,596 | 2/1989 | Hatori | 128/4 |
| 4,899,787 | 2/1990 | Ouchi et al. | 604/282 X |
| 5,035,231 | 7/1991 | Kubokawa et al. | 128/6 |
| 5,152,277 | 10/1992 | Honda et al. | 128/4 |
| 5,170,775 | 12/1992 | Tagami | 128/4 |

FOREIGN PATENT DOCUMENTS

| | | |
|---|---|---|
| 2059574A | 6/1971 | Germany. |
| 3602092A | 8/1986 | Germany. |
| 55-112505 | 8/1980 | Japan. |
| 63-77003 | 5/1988 | Japan. |

*Primary Examiner*—Richard J. Apley
*Assistant Examiner*—Beverly A. Meindl
*Attorney, Agent, or Firm*—Fish & Richardson

[57] ABSTRACT

A protective tube covering an insertion portion of an endoscope is shorter than an inner structure of the insertion portion, and a protective tube covering a bending portion is longer than an inner structure of the bending portion. The front end of the protective tube of the insertion portion, as well as the rear end of the protective tube of the bending portion, is disposed a predetermined distance rearwardly from a portion of connection between the inner structure of the insertion portion and the inner structure of the bending portion. The protective tube of the bending portion covers not only the inner structure of the bending portion but also the above connection portion and the front end portion of the inner structure of the insertion portion. Since the protective tube of the bending portion is softer than the protective tube of the insertion portion, the front end portion of the insertion portion covered by the former protective tube is more flexible and bendable than the other portion of the insertion portion, and serves as an insertion guide portion. In order to restrain a slack of the protective tube of the bending portion, a portion of this protective tube intermediate the opposite ends thereof is fixed to the outer periphery of at least one of the inner structure of the insertion portion, the inner structure of the bending portion and the connection portion.

9 Claims, 4 Drawing Sheets

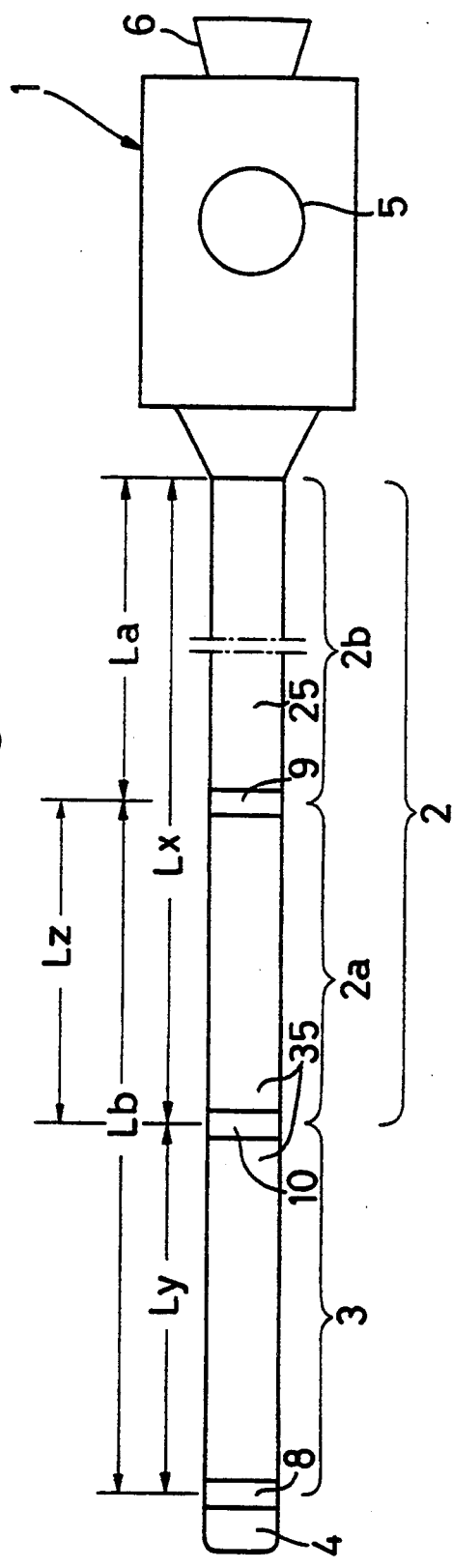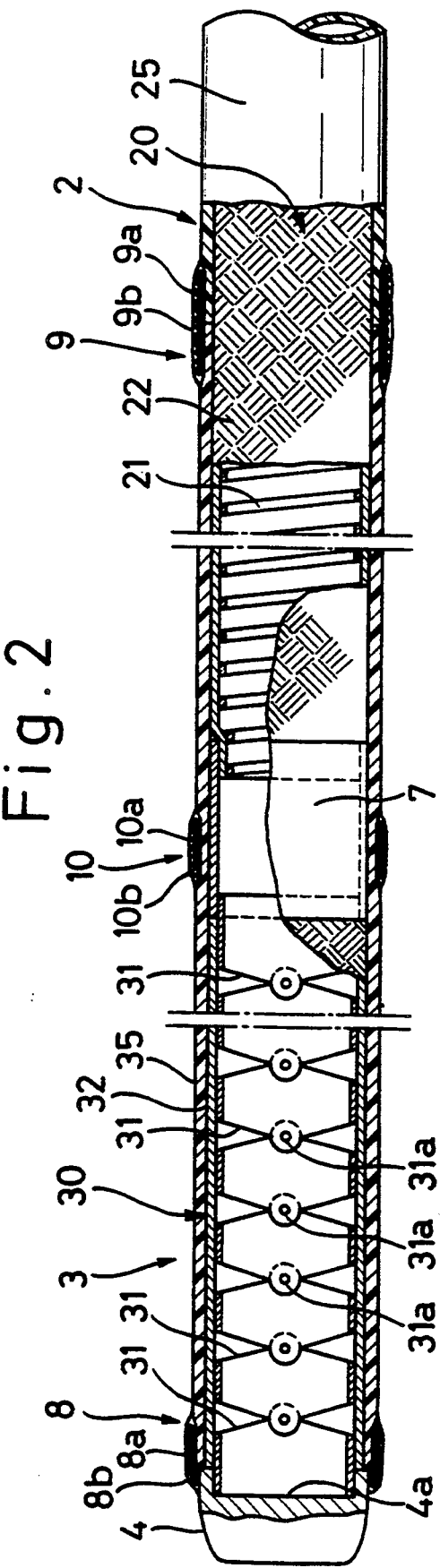

ENDOSCOPE

BACKGROUND OF THE INVENTION

This invention relates to an endoscope.

An endoscope comprises a body, an insertion portion extending from the body, a bending portion extending from a front end of the insertion portion, and a rigid tip member mounted on a front end of the bending portion. The bending portion is remotely operated or bent by manipulating a manipulation member mounted on the body.

Generally, the insertion portion comprises a spiral member, a first braid mounted around the spiral member, and a first protective tube mounted around the first braid. Generally, the bending portion comprises a row of ring-shaped segments pivotally connected to one another, a second braid mounted around the row of ring-shaped segments, and a second protective tube mounted around the second braid. The foremost one of the row of segments is fixedly secured to the tip member, and the rearmost segment is connected to the spiral member of the insertion portion via a connecting ring.

The insertion portion, though flexible or soft, needs to have a certain degree of rigidity. If the insertion portion is too soft, it is contracted upon receipt of an axial compression force, so that the insertion portion fails to advance along a body cavity. On the other hand, the bending portion need to be more flexible than the insertion portion, because the bending portion is required to be bent into a large angle with a relatively small manipulating force from the manipulation member. For this reason, the second braid is softer than the first braid, and the second protective tube is softer than the first protective tube.

Generally, the front end of the first protective tube and the rear end of the second protective tube are held in contact with each other at the outer peripheral surface of the above-mentioned connecting ring. Each of these protective tubes is fixedly secured to the connecting ring by a yarn wound on the end of the protective tube.

In the endoscope of an above general construction, the relatively rigid insertion portion and the relatively soft bending portion are directly connected together, so that a point of abrupt change in rigidity exists in this connection portion. Therefore, when the portion of connection between the bending portion and the insertion portion is abutted against a curved portion of a body cavity of a patient during the insertion of the endoscope into the body cavity, the front end portion of the insertion portion close to the connection portion can not be bent smoothly, thus giving a pain to the patient.

In an endoscope disclosed in Japanese Laid-Open Utility Model Application No. 55-112505, an insertion portion and a bending portion have a common protective tube. This protective tube comprises two layers made respectively of soft resins. The resin of the inner layer is softer than the resin of the outer layer. The outer layer is thickest at its proximal end adjacent to a body, and is decreasing in thickness progressively toward its distal end. On the other hand, the inner layer is thinnest at its proximal end, and is increasing in thickness progressively toward its distal end. The sum of the thicknesses of the two layers is uniform over the entire length of the protective tube. With the use of this protective tube, the rigidity over the area from the insertion portion to the bending portion continuously varies, and therefore it is thought that the insertion of the endoscope into a body cavity can be carried out smoothly, thus giving less pain to the patient. However, the use of such a protective tube increases the cost of a endoscope. Further, a relatively long portion of the protective tube close to the distal end is soft, and therefore the slack of this relatively long portion is increased by the repeated wiping and rinsing of the protective tube after the diagnosis and by the repeated bending of the bending portion by the manipulation member. This slack gives a pain to the patient when the bending portion and the insertion portion are to be inserted into the body cavity.

Japanese Laid-Open Utility Model Application No. 63-77003 discloses an endoscope related to the present invention. In this endoscope, a second protective tube of a bending portion covers the entire outer periphery of a connecting ring connecting a spiral member of an insertion portion to a rear segment of the bending portion, and the rear end portion of this second protective tube extends slightly rearwardly from the connecting ring. At a position rearwardly of and adjacent to the connecting ring, the rear end portion of the second protective tube of the bending portion, as well as a front end portion of a first protective tube of the insertion portion, is fixedly secured to the outer periphery of a first braid of the insertion portion. This fixing is effected by winding a yarn on the outer peripheries of the end portions of the first and second protective tubes. In this endoscope, since the rear end portion of the second protective tube is fixed at a position adjacent to the connecting ring, the front end portion of the insertion portion (which is disposed rearwardly of the connection portion) is not softer than the other portion of the insertion portion. Therefore, this endoscope does not have the advantages of the present invention.

SUMMARY OF THE INVENTION

It is an object of this invention to provide an endoscope which can be easily inserted into a body cavity of a patient, and prevents a slack of a protective tube.

According to the present invention, there is provided an endoscope comprising:

(a) a body having a manipulation member mounted thereon;

(b) an insertion portion extending from the body, the insertion portion comprising a first inner structure of a tubular shape, and a first protective tube covering the first inner structure, and the first inner structure determining the length of the insertion portion;

(c) a bending portion extending from a front end of the insertion portion, the bending portion being remotely bendable by the manipulation member, the bending portion comprising a second inner structure of a tubular shape, and a second protective tube covering the second inner structure, the second inner structure determining the length of the bending portion, the second protective tube being softer than the first protective tube, and a front end of the first inner structure and a rear end of the second inner structure being connected together to provide a connection portion; and (d) a rigid tip member mounted on a front end of the bending portion;

(e) wherein the second protective tube is longer than the second inner structure, and a rear end of the second protective tube is disposed a predetermined distance rearwardly from the connection portion; the first protective tube is shorter than the first inner structure, and a front end of the first protective tube is disposed at generally the same position as the rear end of the second protective tube; the second protective tube covers the whole of the second inner structure, the connection portion and a front end portion of the first inner structure; a front end portion of the insertion portion covered by the second protective tube is more flexible and bendable than the other portion of the insertion portion, and serves as an insertion guide portion; a front end portion of the second protective tube is fixed to an outer periphery of at least one of the tip member and a front end portion of the second inner structure; a rear end portion of the second protective tube is fixed to an outer periphery of the first inner structure; and an intermediate portion of the second protective tube intermediate the opposite ends thereof is fixed to the outer periphery of at least one of the first and second inner structures and the connection portion.

BRIEF DESCRIPTION OF THE DRAWINGS

FIG. 1 is a side-elevational view showing an overall construction of an endoscope according to the present invention;

FIG. 2 is an enlarged cross-sectional view showing a front end portion of an insertion portion and a bending portion of the endoscope;

DESCRIPTION OF THE PREFERRED EMBODIMENTS

Figure 3:
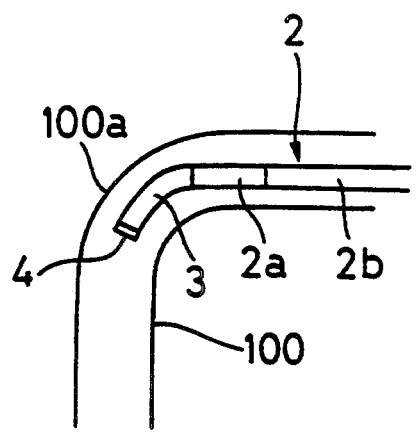
FIGS. 3 to 6 are schematic views showing the sequence of insertion of the endoscope into a body cavity.

One preferred embodiment of the present invention now be described with reference to FIGS. 1 to 7. As shown FIG. 1, an endoscope comprises a body 1, an insertion portion 2 extending from the body 1, a bending portion 3 extending from a front end of the insertion portion 2, and a rigid tip member 4 mounted on a front end of the bending portion 3. The insertion portion 2, as well as the bending portion 3, is so flexible as to be bent. As is well known, the bending portion 3 is connected to a manipulation member 5, mounted on the body 1, by wires passing through the insertion portion 2 and the bending portion 3, and is remotely operated or bent by manipulating the manipulation member 5. An illumination window and an inspection window (both of which are not shown) are formed in the tip member 4. As is well known, the illumination window is connected to a light source by an optical fiber passing through the bending portion 3, the insertion portion 2, the body 1 and a cable (which is not shown and extends from the body 1). With this arrangement, light from the light source is supplied to a body cavity through the illumination window. As is well known, the inspection window is optically connected to an ocular portion 6, mounted on the body 1, by an optical system including an optical fiber, and with this arrangement the body cavity can be observed from the ocular portion 6. The endoscope may be of the type connectable to a television.

As shown in FIG. 2, the insertion portion 2 comprises a first inner structure 20 of a tubular shape, and a first protective tube 25 covering this inner structure 20. The first inner structure 20 comprises a spiral member 21 formed by spirally winding a strip, and a first braid 22 covering the spiral member 21. The first protective tube 25 is fitted on the outer periphery of the first braid 22.

The bending portion 3 comprises a second inner structure 30 of a tubular shape, and a second protective tube 35 covering the second inner structure 30. The second inner structure 30 comprises a row of ring-shaped segments 31 connected to one another, and a second braid 32 covering the row of the segments 31. The second protective tube 35 is fitted on the outer periphery of the second braid 32. Any two adjacent segments 31 are pivotally connected together by a pair of pins 31a which are disposed in diametrically opposite relation to each other. Two guides (not shown) are provided respectively on two diametrically-opposite portions of the inner periphery of each segment 31 which are circumferentially spaced 90° from the pins 31a, and a pair of operating wires for remote manipulation purposes are passed respectively through tile two rows of aligned guides. The proximal ends of the operating wires are connected to the manipulation member 5, and the distal ends of the operating wires are fixedly secured to the inner peripheral surface of the foremost segment 31. Therefore, when one of the operating wires is pulled by manipulating the manipulation member 5, the bending portion 3 is bent downwardly, and when the other operating wire is pulled, the bending portion 3 is bent upwardly.

As shown in FIG. 2, the front end of the second inner structure 30 of the bending portion 3 is connected to the tip member 4. More specifically, the foremost one of tile row of segments 31 is fitted in a recess 4a formed in the rear end of the tip member 4, and connected thereto by brazing or the like.

Figure 7:
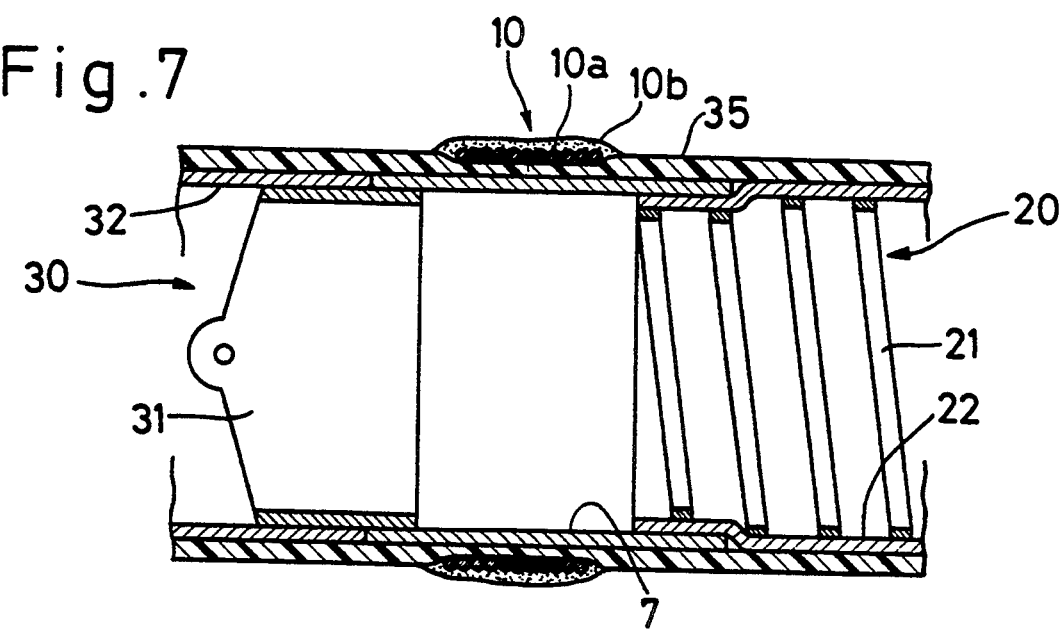
FIG. 7 is a cross-sectional view of a portion of connection between the insertion portion and the bending portion of the endoscope.

As shown in FIGS. 2 and 7, the rear end portion of the second inner structure 30 of the bending portion 3 is connected to the front end portion of the first inner structure 20 of the insertion portion 2. More specifically, a connecting ring 7 of a cylindrical shape is used to achieve this connection. The rearmost one of the row of segments 31 is fitted in the front end portion of the connecting ring 7, and is connected thereto by brazing or the like. On the other hand, the front end portion of the spiral member 21, as well as the front end portion of the first braid 22, is reduced in diameter, and this reduced-diameter portion is fitted in the rear end portion of the connecting ring 7, and is connected thereto by brazing or the like.

The first braid 22 is connected to the spiral member 21 only at its front and rear end portions, and the other portion of the first braid 22 is not fixedly connected to the spiral member 21, but is merely held in contact therewith. The front end portion of the second braid 32 is fixedly secured to the outer periphery of the foremost segment 31, and the rear end portion of the second braid 32 is fixedly secured to the outer periphery of the rearmost segment 31. The other portion of the second braid 32 is not fixedly secured to the other segments 31 intermediate the foremost and rearmost segments 31, but is merely held in contact with the other segments 31. The second braid 32 is softer (more flexible) than the first braid 22.

Next, the first protective tube 25 and the second protective tube 35 which constitute features of the present invention will now be described. The first protective tube 25 is made of a heat-shrinkable, soft resin (e.g., urethane rubber), and is heat-shrunk to fit on the outer periphery of the first braid 22, so that the first protective tube 25 is substantially integral with the first braid 22, and is not movable relative thereto. As shown in FIG. 1, the length La of the first protective tube 25 shorter than the length Lx of the first inner structure 20. Therefore, the front end of the first protective tube 25 spaced a predetermined distance Lz rearwardly from the connecting ring 7. The length Lx of the first inner structure 20 is recognized as the length of the insertion portion 2.

The second protective tube 35 is made, for example, of fluororubber, and is softer than the first protective tube 25. The length Lb of the second protective tube 35 is longer by an amount Lz than the length Ly of the second inner structure 20. Therefore, the second protective tube 35 covers the whole of the second inner structure 30 of the bending portion 3, and also covers the connecting ring 7 and the front end portion of the first inner structure 20 of the insertion portion 2. The rear end of the second protective tube 35 is disposed at generally the same position as the front end of the first protective tube 25. The length Ly of the second inner structure 30 is recognized as the length of the bending portion 3.

The front end of the second protective tube 35 is held in contact with the rear end of the tip member 4. A yarn or thread 8a of nylon is tightly wound around the outer periphery of the rear end portion of the tip member 4 and the outer periphery of the front end portion of the second protective tube 35, so that the front end portion of the second protective tube 35 is fixed to the outer periphery of the foremost segment 31 through the second braid 32, and is also fixed to the tip member 4.

A nylon yarn 9a is tightly wound around the outer periphery of the rear end portion of the second protective tube 35 and the outer periphery of the front end portion of the first protective tube 25, so that the rear end portion of the second protective tube 35 is fixed to the first inner structure 20 of the insertion portion 2 and the front end portion of the first protective tube 25.

As shown in FIGS. 2 and 7, a nylon yarn 10a is tightly wound around the outer periphery of an intermediate portion of the second protective tube 35 to fix this intermediate portion to the outer periphery of the connecting ring 7.

Coatings 8b, 9b and 10b (e.g. polyurethane coating) are applied respectively to the nylon yarns 8a, 9a and 10a to prevent the untying thereof, and therefore these coatings cooperate respectively with the nylon yarns 8a, 9a 10a to constitute fixing means 8, 9 and 10, respectively.

The second protective tube 35 is not fixed to the outer periphery of the first braid 22 and the outer periphery of the second braid 32, but are merely held in contact therewith except for those portions of this tube 35 fixed respectively by the fixing means 8, 9 and 10. Therefore, the second protective tube 35 is movable relative to the first and second braids 22 and 32 except for the above-mentioned portions thereof.

The front end portion 2a of the insertion portion 2 having the length Lz is covered not by the first protective tube 25, but by the second protective tube 35 softer than the first protective tube 25. The second protective tube 35 is not fixed to the first braid 22 except for the rear end portion thereof. Therefore, the front end portion 2a is softer than the other portion 2b of the insertion portion 2, and serves as an insertion guide portion as later described.

In order to smoothly guide the endoscope into a body cavity as later described, it is preferred that the length Lz of the insertion guide portion 2a should be more than 50% of the length Ly of the bending portion 3, and be less than 150% of the length Ly of the bending portion 3. In this embodiment, the length Ly of the bending portion 3 is 35 mm, and the length Lz of the insertion guide portion 2a is 30 mm, and the sum of the lengths (Lx+Ly) of the insertion portion 2 and the bending portion 3 is 300 to 500 mm.

Figure 4:
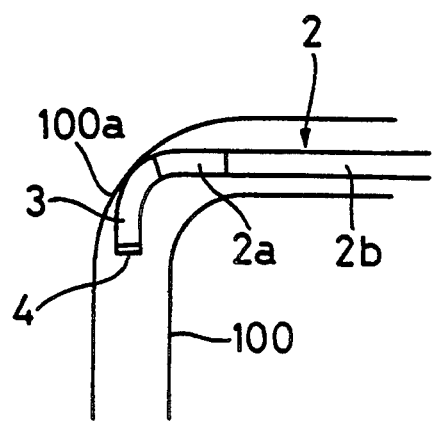
Figure 5:
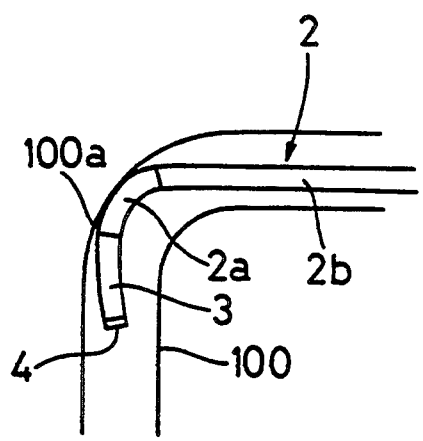
Figure 6:
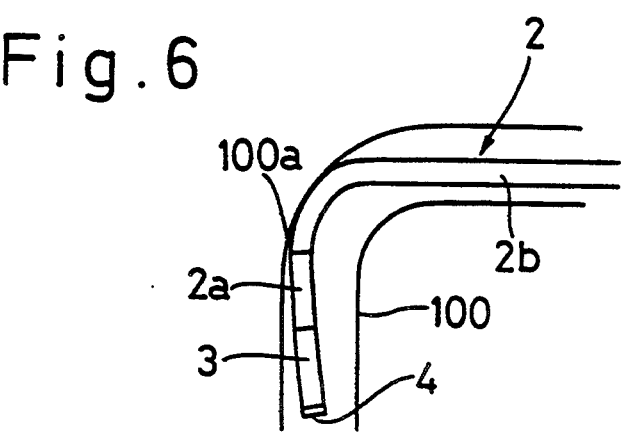

The bending portion 3 and the insertion portion 2 of the above endoscope are inserted into a body cavity 100 in a manner as shown in FIGS. 3 to 6. More specifically, as shown in FIG. 3, when the tip member 4 reaches a curved portion 100a of the body cavity 100, the operator manipulates the manipulation member 5 to bend the bending portion 3 into a configuration corresponding to the curved portion 100a. In this condition, when the insertion portion 2 is further inserted, the bending portion 3 is abutted against the curved portion 100a, as shown in FIG. 4. Then, when the insertion portion 2 is further inserted, the insertion guide portion (front end portion) 2a of the insertion portion 2 is bent by the resistance offered by the curved portion 100a, as shown in FIG. 5. The insertion guide portion 2a is softer than the other portion 2b of the insertion portion 2, and therefore can be easily bent. As a result, when the insertion portion 2 is further inserted, the insertion portion 2 can smoothly pass through the curved portion 100a. as shown in FIG. 6.

The second protective tube 35 is longer than a second protective tube of an ordinary endoscope, and therefore if this tube 35 is fixed only at its opposite ends, the second protective tube 35 may be slackened by a repeated wiping and rinsing after a diagnosis and by the repeated bending of the bending portion 3. In the present invention, however, the intermediate portion of the second protective tube 35 is fixed to the outer periphery of the connecting ring 7 by the fixing means 10, and the slack is kept to zero or a minimum, and therefore the patient will not suffer from pain because of such slack.

Other embodiments of the present invention will now be described. Those portions of the following embodiments corresponding to those of the preceding embodiment are designated by identical reference numerals, respectively, and explanation thereof will be omitted.

Figure 8:
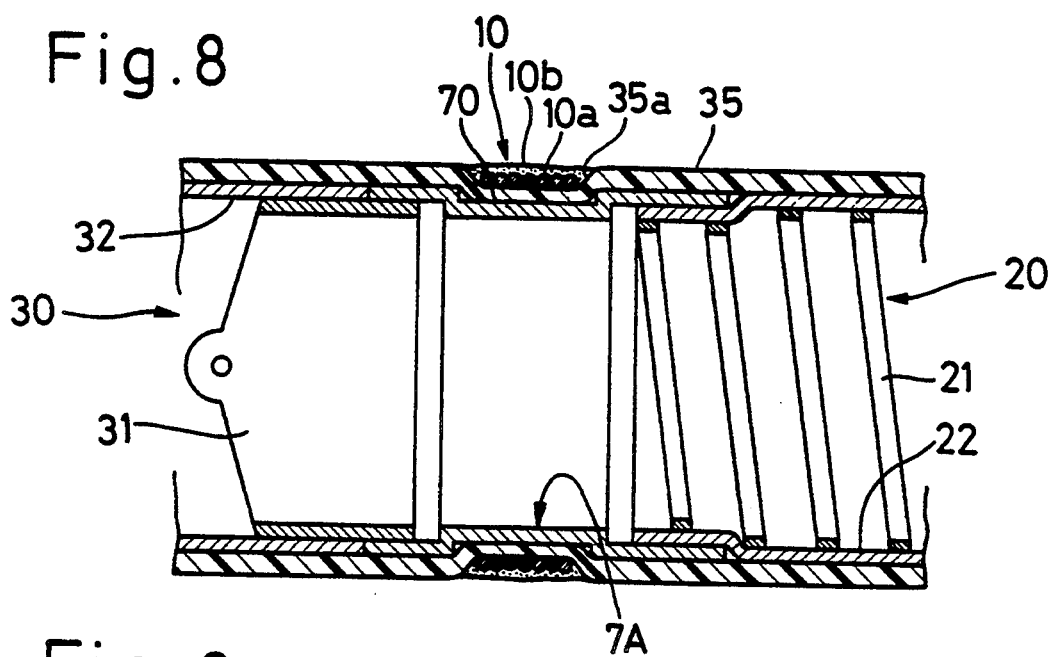
FIG. 8 is a view similar to FIG. 7, but showing a modified form of the invention.

In the embodiment shown in FIG. 8, an annular recess 70 is formed in an outer periphery of a connecting ring 7A intermediate opposite ends thereof. An intermediate portion of a second protective tube 35 is received in the recess 70, and is fixed thereto by fixing means 10 comprising a nylon yarn 10a and a coating 10b. In this fixed condition, an annular recess 35a is also formed in the outer periphery of the second protective tube 35, and the fixing means 10 is received in this recess 35a.

Figure 9:
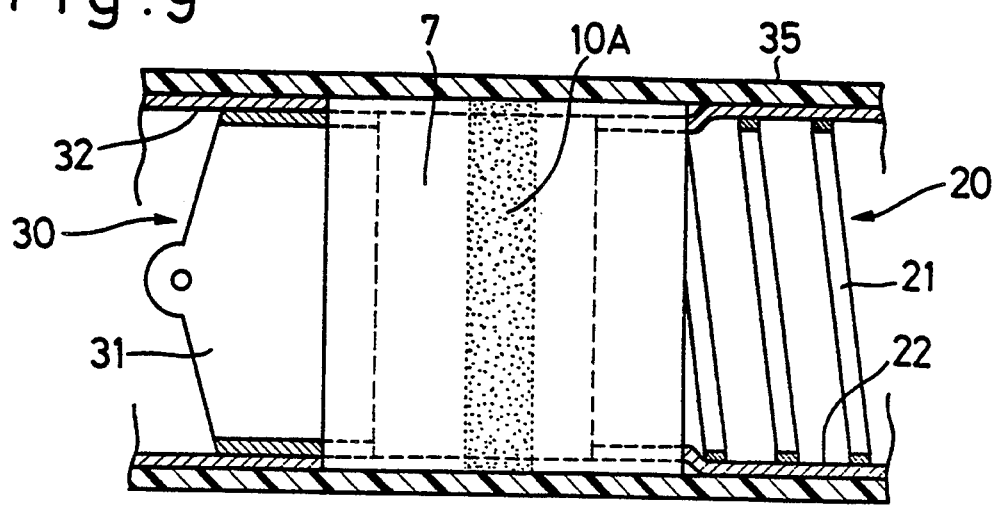
FIG. 9 is a view similar to FIG. 7, showing another modified form of the invention.

In the embodiment shown in FIG. 9, an inner surface of an intermediate portion of a second protective tube 35 is fixed to an outer peripheral surface of a connecting ring 7 by an adhesive (e.g., hot-melt adhesive) 10A.

Figure 10:
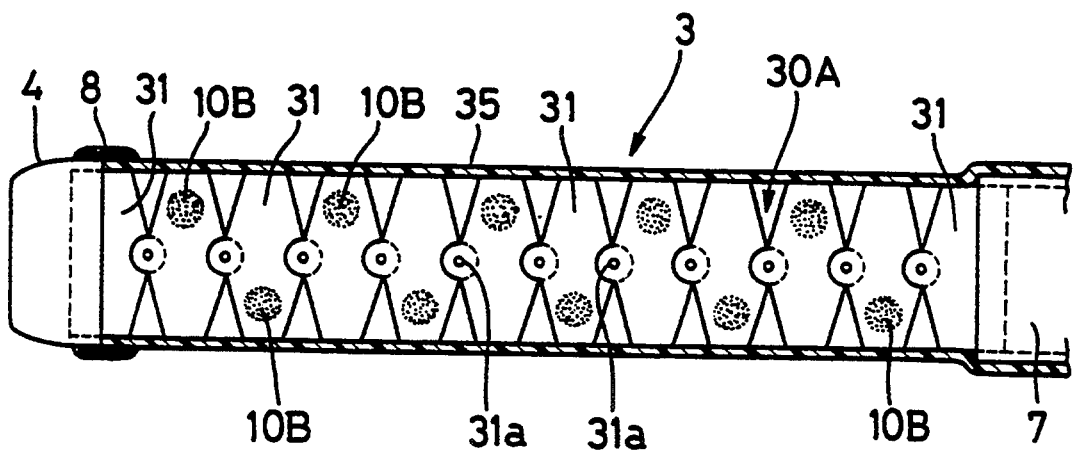
FIG. 10 is a cross-sectional view showing a modified bending portion.

In the embodiment shown in FIG. 10, an inner structure 30A of a bending portion 3 is constituted only by a row of segments 31 connected together, and a second protective tube 35 is fitted directly on the row of segments 31 without the use of a braid therebetween. An inner surface of an intermediate portion of the second protective tube 35 is fixed to two portions of the outer periphery of each of the segments 31 by an adhesive 10B. The fixed portions of the segments 31 by the adhesive 10B are disposed alternately on the upper side and lower side (FIG. 10) of a plane in which pins 31a lie. With this arrangement, the reduction of the flexibility of the second protective tube 35 due to the fixing of the second protective tube 35 to the segments 31 can be restrained. All the segments 31 may be fixed at the outer peripheries of those portions thereof intersecting a plane in which the pins 31a lie.

Figure 11:
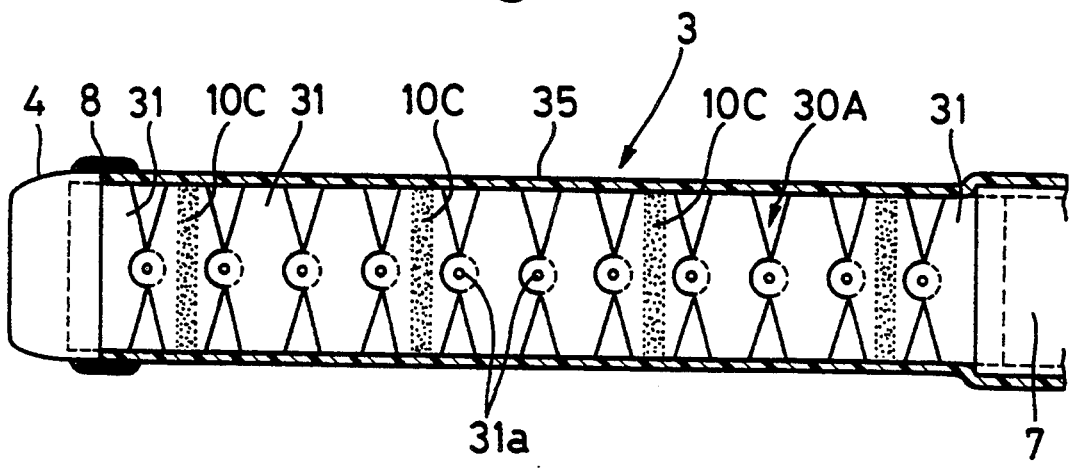
FIG. 11 is view similar to FIG. 10, showing another modified bending portion.

In the embodiment shown in FIG. 11, an inner peripheral surface of an intermediate portion of a second protective tube 35 is bonded by an adhesive 10C to those of a row of segments 31 disposed at predetermined intervals, the inner peripheral surface of this intermediate portion being bonded to the entire outer periphery of each of said those segments 31. Only a generally central one of the row of segments 31 may be fixed to the intermediate portion of the second protective tube 35.

In the embodiments shown in FIGS. 10 and 11, the intermediate portion of the second protective tube 35 may or may not be fixed to the connecting ring 7.

The intermediate portion of the second protective tube may be fixed to the outer periphery of the first braid (designated at 22 in FIGS. 2 and 7), in which case this intermediate portion may or may not be fixed to the segments and the connecting ring.

What is claimed is:

1. An endoscope comprising:
   (a) a body having a manipulation member mounted thereon;
   (b) an insertion portion extending from said body, said insertion portion comprising a first inner structure of a tubular shape, and a first protective tube covering said first inner structure, and said first inner structure determining the length of said insertion portion;
   (c) a bending portion extending from a front end of said insertion portion, said bending portion being remotely bendable by said manipulation member, said bending portion comprising a second inner structure of a tubular shape, and a second protective tube covering said second inner structure, said second inner structure determining the length of said bending portion, said second protective tube being softer than said first protective tube, and a front end of said first inner structure and a rear end of said second inner structure being connected together to provide a connection portion; and
   (d) a rigid tip member mounted on a front end of said bending portion;
   (e) wherein said second protective tube is longer than said second inner structure, and a rear end of said second protective tube is disposed a predetermined distance rearwardly from said connection portion; said first protective tube is shorter than said first inner structure, and a front end of said first protective tube is disposed at generally the same position as the rear end of said second protective tube; said second protective tube covers the whole of said second inner structure, said connection portion and a front end portion of said first inner structure; a front end portion of said insertion portion covered by said second protective tube is more flexible and bendable than the other portion of said insertion portion, and serves as an insertion guide portion; a front end portion of said second protective tube is fixed to an outer periphery of at least one of said tip member and a front end portion of said second inner structure; a rear end portion of said second protective tube is fixed to an outer periphery of said first inner structure; an intermediate portion of said second protective tube intermediate the opposite ends thereof if fixed to the outer periphery of at least one of said first and second inner structures and said connection portion; and said insertion guide portion is sufficiently long so that said insertion guide portion can be easily bent when said bending portion is abutted against a curved portion of a body cavity.

2. An endoscope according to claim 1, wherein the length of said insertion guide portion is more than 50% of the length of said bending portion and is less than 150% of the length of said bending portion.

3. An endoscope according to claim 1, in which said intermediate portion of said second protective tube is fixed only to the outer periphery of said connection portion between said first and second inner structures.

4. An endoscope according to claim 1, in which said connection portion has a connecting ring, the rear end portion of said second inner structure being fitted in and fixed to a front end portion of said connecting ring, the front end portion of said first inner structure being fitted in and fixed to a rear end portion of said connecting ring, and said intermediate portion of said second protective tube being fixed to an outer periphery of said connecting ring.

5. An endoscope according to claim 4, in which said second protective tube is fixed to the outer periphery of said connecting ring by a yarn wound around the outer periphery of said second protective tube.

6. An endoscope according to claim 5, wherein an annular recess is formed in the outer peripheral surface of said connecting ring, a first portion of said second protective tube disposed in registry with said annular recess being fixed to said connecting ring by said yarn, and said yarn being received in a recess formed in the outer periphery of said first portion of said second protective tube disposed in registry with said recess in said connecting ring.

7. An endoscope according to claim 4, in which said intermediate portion of said second protective tube is fixed by an adhesive provided between the inner peripheral surface of said intermediate portion and the outer peripheral surface of said connecting ring.

8. An endoscope according to claim 1, in which said second inner structure of said bending portion comprises a row of segments pivotally connected to one another, said intermediate portion of said second protective tube being fixed to an outer periphery of at least one of said segments by an adhesive.

9. An endoscope comprising:
   (a) a body having a manipulation member mounted thereon;
   (b) an insertion portion extending from said body, said insertion portion comprising a first inner structure of a tubular shape, and a first protective tube covering said first inner structure, and said first inner structure determining the length of said insertion portion;
   (c) a bending portion extending from a front end of said insertion portion, said bending portion being remotely bendable by said manipulation member, said bending portion comprising a second inner structure of a tubular shape, said second inner structure comprising a row of connected ring-shaped segments and a braid covering said row of segments, and a second protective tube covering said second inner structure, said second inner structure determining the length of said bending portion, said second protective tube being softer than said first protective tube, and a front end of said first inner structure and a rear end of said second inner structure being connected together to provide a connection portion; and (d) a rigid tip member mounted on a front end of said bending portion;

(e) wherein said second protective tube is longer than said second inner structure, and a rear end of said second protective tube is disposed a predetermined distance rearwardly from said connection portion; said first protective tube is shorter than said first inner structure, and a front end of said first protective tube is disposed at generally the same position as the rear end of said second protective tube; said second protective tube covers the whole of said second inner structure, said connection portion and a front end portion of said first inner structure; a front end portion of said insertion portion covered by said second protective tube is more flexible and bendable than the other portion of said insertion portion, and serves as an insertion guide portion; a front end portion of said second protective tube is fixed to an outer periphery of at least one of said tip member and a front end portion of said second inner structure; a rear end portion of said second protective tube is fixed to an outer periphery of said first inner structure; an intermediate portion of said second protective tube intermediate the opposite ends thereof is fixed to the outer periphery of at least one of said first and second inner structures and said connection portion; and said insertion guide portion is sufficiently long so that said insertion guide portion can be easily bent when said bending portion is abutted against a curved portion of a body cavity.

* * * * *

UNITED STATES PATENT AND TRADEMARK OFFICE
CERTIFICATE OF CORRECTION

PATENT NO. : 5,386,816

DATED : February 7, 1995

INVENTOR(S) : Masahiro INOUE, Kunihiko MIYAGI

It is certified that error appears in the above-identified patent and that said Letters Patent is hereby corrected as shown below:

Column 8, line 9, change "if" to --is--.

Signed and Sealed this

Twenty-sixth Day of September, 1995

Attest:

BRUCE LEHMAN

Attesting Officer

Commissioner of Patents and Trademarks